(12) United States Patent
Wang et al.

(10) Patent No.: US 8,314,076 B2
(45) Date of Patent: *Nov. 20, 2012

(54) METHOD FOR INHIBITING SCAVENGER RECEPTOR-A AND INCREASING IMMUNE RESPONSE TO ANTIGENS

(75) Inventors: Xiang-Yang Wang, Amherst, NY (US); John Subjeck, Williamsville, NY (US)

(73) Assignee: Health Research Inc., Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,177

(22) Filed: Mar. 6, 2012

(65) Prior Publication Data
US 2012/0156223 A1   Jun. 21, 2012

Related U.S. Application Data

(62) Division of application No. 12/104,105, filed on Apr. 16, 2008, now Pat. No. 8,133,875.

(60) Provisional application No. 60/923,628, filed on Apr. 16, 2007.

(51) Int. Cl.
  C07H 21/02 (2006.01)
  C07H 21/04 (2006.01)
  A61K 31/70 (2006.01)
(52) U.S. Cl. ............... 514/44 A; 536/24.1; 536/24.5
(58) Field of Classification Search ............ 514/44; 536/24.4, 24.5
  See application file for complete search history.

Primary Examiner — Terra Cotta Gibbs
(74) Attorney, Agent, or Firm — Hodgson Russ LLP

(57) ABSTRACT

Provided is a method for enhancing an immune response to a desired antigen in an individual. The method is performed by administering to the individual an agent capable of inhibiting class A macrophage scavenger receptor (SR-A) and optionally administering the desired antigen. Also provided is a method for enhancing an immune response to an antigen by administering to an individual a composition containing antigen presenting cells that are characterized by specifically inhibited SR-A. Substantially purified populations of mammalian dendritic cells characterized by specifically inhibited SR-A are also provided.

7 Claims, 9 Drawing Sheets

METHOD FOR INHIBITING SCAVENGER RECEPTOR-A AND INCREASING IMMUNE RESPONSE TO ANTIGENS

This application is a divisional of U.S. application Ser. No. 12/104,105, filed Apr. 16, 2008, now U.S. Pat. No. 8,133,875 which claims priority to U.S. application Ser. No. 60/923,628, filed on Apr. 16, 2007, the disclosures of each of which are incorporated herein by reference.

This work was supported by funding from the National Institutes of Health Grant No. RO1 CA129111, CA 099326 and R21 CA121848. The Government has certain rights in the invention.

FIELD OF THE INVENTION

The present invention relates to the general field of immunotherapy and more particularly provides a method for increasing an immune response to an antigen.

RELATED ART

The class A macrophage scavenger receptor (SR-A) is expressed primarily by macrophage (Mϕ), which are among the first line of anti-microbial defense (1). SR-A is the prototypic member of an expanding family of structurally diverse membrane receptors collectively termed scavenger receptors (2, 3). Receptors of this group recognize a number of ligands, including chemically modified or altered molecules, endoplasmic reticulum (ER) resident chaperones, as well as the modified lipoproteins that are pertinent to the development of vascular disease (3-5). SR-A was originally identified as a clearance receptor for acetylated low-density lipoprotein (acLDL) (3, 6) and studies of its involvement in atherosclerosis remain dominant because of its relationship to this disease. However, it has also been shown that lipopolysaccharide (LPS) of Gram negative and lipoteichoic acid of Gram positive bacteria compete with binding of other known SR-A ligands, which and indicates that SR-A functions as a pattern recognition receptor (2). In this regard, Suzuki et al. originally reported that SR-A$^{-/-}$ mice have impaired protection against infection by *Listeria monocytogenes* and herpes simplex virus (7). Independent studies by others also indicate that expression of SR-A may be of importance in mounting immune responses against bacterial infection (8-10). However, despite the availability of information about SR-A in atherosclerosis and in pathogen recognition, very little is known about its role in acquired immunity, and there is thus an ongoing need to develop techniques that entail modulating SR-A to improve immunological responses.

SUMMARY OF THE INVENTION

The present invention provides a method for enhancing an immune response to a desired antigen in an individual. The method comprises administering to the individual a desired antigen and an agent capable of inhibiting class A macrophage scavenger receptor (SR-A). By administering the agent and the antigen to the individual, the immune response to the antigen in the individual is enhanced.

In another embodiment, a method is provided for enhancing an immune response to a tumor in an individual. The method comprising administering to the individual, in an amount effective to enhance an immune response to the tumor, an agent capable of inhibiting class A macrophage scavenger receptor (SR-A), wherein the growth of the tumor is inhibited subsequent to administering the agent. The method may further comprise administering to the individual an antigen that is expressed by the tumor.

The agent may be any composition of matter that can specfically inhibit SR-A. Examples of such agents include but are not limited to polynucleotides that interfere with transcription and/or translation of SR-A mRNA. The agent may also be an antibody that binds to and antagonizes SR-A. The agent may also be any of various known sulfonamidobenzanilide compounds that can be used as SR-A antagonists.

Also provided is a method for enhancing an immune response to a desired antigen comprising administering to an individual a composition comprising dendritic cells, wherein the dendritic cells are characterized by specifically inhibited SR-A. The method may further comprise exposing the dendritic cells to the desired antigen in vitro prior to administration to the individual.

The invention also provides a composition comprising a substantially purified population of mammalian dendritic cells, wherein the dendritic cells are characterized by specifically inhibited SR-A activity.

BRIEF DESCRIPTION OF THE FIGURES

FIG. 7A: Day-7: bone-marrow derived dendritic cells (BM-DCs) from WT or SR-A$^{-/-}$ C57BL/6 mice were pulsed with OVA protein (10 µg/ml) for 6 h, and subsequently stimulated with LPS (10 ng/ml) overnight. WT C57BL/6 mice (n=6) were vaccinated with antigen-loaded WT or SR-A$^{-/-}$ DCs (1×10$^6$ cells per mouse) twice at weekly intervals, followed by tumor challenge with 1×10$^5$ B16-OVA melanoma cells. FIG. 7B: WT C57BL/6 mice were immunized with OVA protein-pulsed WT or SR-A$^{-/-}$ BM-DCs twice at weekly intervals. One week after the second vaccination, splenocytes were harvested and stimulated with OVA-specific MHC I-restricted CTL epitope OVA$_{257-264}$ (1 µg/ml) in the presence of IL-2. The number of IFN-γ producing cells was measured using ELISPOT assays.

FIG. 8A: DC1.2 cells (1×10$^6$ cells per well) were transfected with LV-SRA-shRNA, LV-Scramble-shRNA at a MOI of 10 or left untreated. Cells were harvested 2 days later and subjected to immunoblotting. β-actin was used as a control. FIG. 8B: DC cells were harvested 2 days after infection and pulsed with OVA protein (10 µg/ml) for 3 h. Following stimulation with LPS (10 ng/ml) overnight, DCs were washed extensively and injected to mice subcutaneously. The vaccination was repeated one week later. Mice were challenged with B16-OVA one week after the second immunization.

FIG. 9A: C57BL/6 mice were immunized with LV-scramble-shRNA or LV-SRA-shRNA infected DC1.2 cells. Splenocytes were then harvested and stimulated with OVA-specific MHC I-restricted CTL epitope OVA$_{257-264}$. The IFN-γ production was measured using ELISPOT assays. FIG. 9B: Splenocytes from immunized animals were stimulated with OVA$_{257-264}$ for 5 days in the presence of IL-2 and co-cultured with $^{51}$Cr-labeled B16-OVA tumor cells at different ratios. Cytotoxicity of T-effector cells was measured using chromium release assays.

DESCRIPTION OF THE INVENTION

Figure 1:
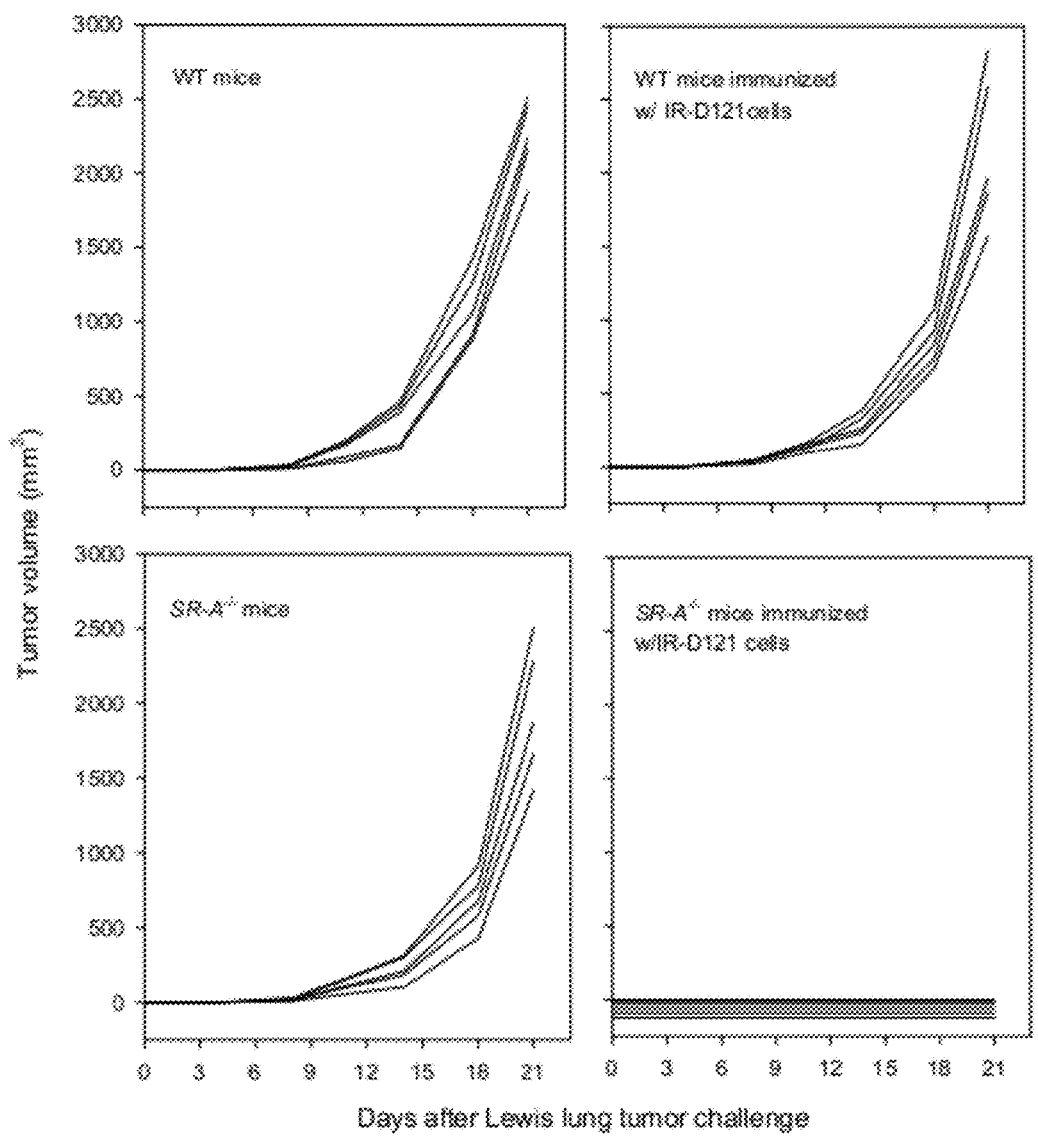
FIG. 1 provides a graphical representation of data obtained from vaccination with ionizing irradiation (IR) treated D121 Lewis lung tumor cells resulting in rejection of poorly immunogenic tumors in SR-A$^{-/-}$ mice. Mice (n=5) were immunized with $^{137}$Cs irradiated D121 cells and challenged with viable D121 tumor cells (4×10$^5$ cells) one week later. Each curve represents tumor growth in each individual mouse (p<0.05, immunized SR-A$^{-/-}$ vs non-immunized SR-A$^{-/-}$ or immunized wild-type (WT) mice). The results shown are from a representative experiment of three performed.

The present invention provides a method for enhancing an immune response to a desired antigen in an individual. The method comprises administering to the individual an agent capable of specifically inhibiting class A macrophage scavenger receptor (SR-A). The agent is administered in an amount effective to enhance an immune response to the antigen in the individual. Thus, the method of the present invention elicits an immune response to a desired antigen in an individual that is greater than if the agent had not been administered. In certain embodiments, the desired antigen may also be administered to the individual.

A "desired antigen" is an antigen to which an enhanced immune response in the individual would be expected to provide a therapeutic benefit. The enhanced immune response may be an enhanced humoral response to the antigen, an enhanced cell mediated response to the antigen, or a combination thereof.

Agents that are capable of specifically inhibiting SR-A are those that interfere with SR-A expression and/or function by binding to SR-A protein or by hybridizing to DNA and/or RNA encoding SR-A. Agents that bind to SR-A can specifically inhibit it by reducing or blocking ligand binding. Agents that hybridize to DNA and/or RNA encoding SR-A can specifically inhibit SR-A by impeding SR-A mRNA transcription and/or translation, and/or by causing degradation of SR-A mRNA.

The invention is based on the discovery of an unexpected role of SR-A in immune response to antigens. In particular, we observed that vaccination of wild type mice (i.e., mice without experimentally altered SR-A expression) with irradiated tumor cells is not effective in eliciting an immune response to the tumor cells, but such vaccination is able to provide long-lasting immunity to subsequent challenge with the tumor cells in SR-A deficient (SR-A –/–) mice. This effect was demonstrated against the poorly immunogenic tumors D121 Lewis lung carcinoma and B16 melanoma. Furthermore, administration of irradiated tumor cells was capable of reducing established tumors in the SR-A deficient mice, but not in their wild type counterparts. Importantly, we also demonstrate that the enhanced immune response to an antigen observed in SR-A –/– mice can be replicated by specific inhibition of SR-A in wild type mice. To demonstrate this, we isolated dendritic cells (DCs) from wild type (SR-A +/+) mice, inhibited SR-A in the DCs using an RNAi strategy, loaded the DCs with the model antigen ovalbumin (OVA), delivered the DCs back to the mice, and challenged the mice with OVA-expressing B16 melanoma cells. By using this technique, no tumors were detected in the treated mice at 36 days after tumor challenge, while 100% of the mice in the negative control group had tumors within 18 days after challenge. We also demonstrated that SR-A down-regulation in DCs promotes an antigen-specific CTL response more effectively than in a negative control. Thus, we have discovered that specific inhibition of SR-A in antigen-presenting cells (e.g., dendritic cells) can reverse unresponsive or weakly responsive immune reactions to poorly immunogenic antigens, and our data indicate that the enhanced antigen-specific CTL response in mice is important to the interaction of SR-A receptor with respect to both innate and adaptive immunity. Thus, it is considered that the present invention provides a method for enhancing immunity to any desired antigen.

Any agent capable of inhibiting SR-A may be used in the method of the invention. For example, the agent may be a polynucleotide that interferes with transcription and/or translation of SR-A mRNA, an antibody that binds to SR-A and inhibits binding to its ligand or otherwise antagonizes the receptor, or any other compound that can specifically inhibit SR-A.

The nucleotide and amino acid sequences of SR-A from different species are known in the art. For example, an mRNA and amino acid sequence of a *Mus musculus* (mouse) SR-A is provided in the National Center for Biotechnology Information (NCBI) database under entry NM 031195 (Jan. 28, 2006 entry). An mRNA and amino acid sequence of a *Homo sapiens* (human) SR-A is provided in the NCBI database under entry BC063878 (Aug. 11, 2006 entry). These mouse and human SR-A sequences share 46% nucleotide homology and 70% amino acid homology.

It is recognized in the art that there are three SR-A isotypes. Isotype 1 and 2 are derived from mRNA splicing, while isotype 3 is believed to be a non-functional SR-A present in the endoplasmic reticulum. It is preferable that the SR-A inhibitor used in the present invention be capable of specifically inhibiting each isotype. In this regard, all three SR-A isotypes are absent in the SR-A deficient mice described herein, and all three isotypes are inhibited by an RNAi strategy employed in demonstrating one embodiment of the invention.

When the agent is a polynucleotide, the agent may be an RNA polynucleotide, a DNA polynucleotide, or a DNA/RNA hybrid. The polynucleotide may be a ribozyme, such as a hammerhead ribozyme, an antisense RNA, an siRNA, a DNAzyme, a hairpin ribozyme, or any modified or unmodified polynucleotide capable of inhibiting SR-A by a process that includes hybridizing to SR-A mRNA or DNA. Methods for designing ribozymes, antisense RNA, siRNA, and DNAzymes are well known in the art. It will be recognized that any such agent will act at least in part via hybridization to RNA or DNA sequences encoding SR-A. Thus, the polynucleotide agents of the present invention will have sufficient length and complementarity with RNA or DNA encoding SR-A so as to hybridize to the RNA or DNA under physiological conditions. In general, at least approximately 10 continuous nucleotides of the polynucleotide agent should be complementary or identical to the SR-A encoding DNA or RNA.

The polynucleotide agent may include modified nucleotides and/or modified nucleotide linkages so as to increase the stability of the polynucleotide. Suitable modifications and methods for making them are well known in the art. Some examples of modified polynucleotide agents for use in the present invention include but are not limited to polynucleotides which comprise modified ribonucleotides or deoxyribonucleotides. For example, modified ribonucleotides may comprise substitutions of the 2' position of the ribose moiety with an —O— lower alkyl group containing 1-6 saturated or unsaturated carbon atoms, or with an —O— aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. The nucleotides may be linked by phosphodiester linkages or by a synthetic linkage, i.e., a linkage other than a phosphodiester linkage. Examples of internucleoside linkages in the polynucleotide agents that can be used in the invention include but are not limited to phosphodiester, alkylphosphonate, phosphorothioate, phosphorodithioate, phosphate ester, alkylphosphonothioate, phosphoramidate, carbamate, carbonate, morpholino, phosphate trister, acetamidate, carboxymethyl ester, or combinations thereof.

In one embodiment, the agent is an siRNA for use in RNA interference (RNAi) mediated silencing or downregulation of SR-A mRNA. RNAi agents are commonly expressed in cells as short hairpin RNAs (shRNA). shRNA is an RNA molecule that contains a sense strand, antisense strand, and a short loop sequence between the sense and antisense fragments. shRNA is exported into the cytoplasm where it is processed by dicer into short interfering RNA (siRNA). siRNA are 21-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of SR-A expression, the polynucleotide agent may be either an siRNA or an shRNA.

shRNA of the invention can be expressed from a recombinant viral vector either as two separate, complementary RNA molecules, or as a single RNA molecule with two complementary regions. In this regard, any viral vector capable of accepting the coding sequences for the shRNA molecule(s) to be expressed can be used. Examples of suitable vectors include but are not limited to vectors derived from adenovirus (AV), adeno-associated virus (AAV), retroviruses (e.g, lentiviruses (LV), Rhabdoviruses, murine leukemia virus), herpes virus, and the like. A preferred virus is a lentivirus. The tropism of the viral vectors can also be modified by pseudotyping the vectors with envelope proteins or other surface antigens from other viruses. One example of an shRNA sequence that is suitable for use in the present invention is provided as SEQ ID NO:1. As an alternative to expression of shRNA in cells from a recombinant vector, chemically stabilized shRNA or siRNs may also be used administered as the agent in the method of the invention.

In another embodiment, the agent may be an antibody that recognizes SR-A. The antibodies used in the invention will accordingly bind to SR-A such that the binding of the antibody interferes with the activity of the SR-A receptor and/or interferes with SR-A ligand binding. It is preferable that the antibody bind to the extracellular region of SR-A, which is known to be present in the C-terminal portion of the receptor, from amino acid positions 125-458.

Antibodies that recognize SR-A for use in the invention can be polyclonal or monoclonal. It is preferable that the antibodies are monoclonal. Methods for making polyclonal and monoclonal antibodies are well known in the art. Additionally, anti-SR-A antibodies are commercially available, such as the 2F8 monoclonal antibody from Serotec (Oxford, UK).

It is expected that antigen-binding fragments of antibodies may be used in the method of the invention. Examples of suitable antibody fragments include Fab, Fab', $F(ab')_2$, and Fv fragments. Various techniques have been developed for the production of antibody fragments and are well known in the art.

It is also expected that the antibodies or antigen binding fragments thereof may be humanized. Methods for humanizing non-human antibodies are also well known in the art (see, for example, Jones et al., *Nature,* 321:522-525 (1986); Riechmann et al., *Nature,* 332:323-327 (1988); Verhoeyen et al., *Science,* 239:1534-1536 (1988)). Other agents that can inhibit SR-A are also known. For example, U.S. Pat. No. 6,458,845 provides a description of a variety of sulfonamidobenzanilide compounds that can be used as SR-A antagonists, and also describes methods for measuring SR-A antagonism. The description of these compounds and methods are incorporated herein by reference.

Compositions comprising an agent that can inhibit SR-A for use in therapeutic purposes may be prepared by mixing the agent with any suitable pharmaceutically acceptable carriers, excipients and/or stabilizers. Some examples of compositions suitable for mixing with the agent can be found in: *Remington: The Science and Practice of Pharmacy* (2005) 21st Edition, Philadelphia, Pa. Lippincott Williams & Wilkins.

If the agent is a polynucleotide, it can be administered to the individual as a naked polynucleotide, in combination with a delivery reagent, or as a recombinant plasmid or viral vector which either comprises or expresses the polynucleotide agent. Suitable delivery reagents for administration include the Mirus Transit TKO lipophilic reagent; lipofectin; lipofectamine; cellfectin; or polycations (e.g., polylysine), or liposomes.

In one embodiment, the polynucleotide is administered to the individual via administration of antigen presenting cells, such as dendritic cells, which comprise the polynucleotide agent.

In general, a formulation for therapeutic use according to the method of the invention comprises an amount of agent effective to enhance an immune response to a desired antigen in the individual. Those skilled in the art will recognize how to formulate dosing regimes for the agents of the invention, taking into account such factors as the molecular makeup of the agent, the size and age of the individual to be treated, and the type and stage of disease. If the desired antigen is also administered to the individual, the desired antigen can be administered prior to, concurrently, or subsequent to administration of the agent via any of the aforementioned routes.

Compositions comprising an agent that inhibits SR-A and which optionally comprise an antigen to which an enhanced immune response is desired can be administered to an individual using any available method and route suitable for drug delivery, including parenteral, subcutaneous, intraperitoneal, intrapulmonary, and intranasal. Parenteral infusions include intramuscular, intravenous, intraarterial, intraperitoneal, and subcutaneous administration.

Administration of the agent with or without the agent can be performed in conjunction with conventional therapies that are intended to treat a disease or disorder associated with the antigen. For example, if the method is used to enhance an immune response to a tumor antigen, the agent can be administered prior to, concurrently, or subsequent to conventional anti-cancer treatment modalities. Such treatment modalities include but are not limited to chemotherapies, surgical interventions, and radiation therapy.

It is expected that an enhanced immune response to any desired antigen could be achieved using the method of the invention. Examples of such antigens include but are not limited to antigens present on infectious organisms and antigens expressed by cancer cells. The desired antigen may be well characterized, but may also be unknown, other than by its known presence in, for example, a lysate from a particular cell type, such as a tumor or bacteria. Antigens useful for the invention may be commercially available or prepared by standard methods.

In one embodiment, the antigen is a tumor antigen. Tumor antigens can be obtained by conventional techniques, such as by preparation of tumor cell lysates by repeatedly freezing and thawing tumor cells/tissues in phosphate buffered saline containing leupeptin and aprotinin (obtained from either fresh tumor biopsy tissues or from tumor cells generated in vitro by tissue culture). Such freezing and thawing results in lysis of cells. The tumor lysate can be obtained by centrifugation and harvesting the supernatant fluid. The tumor cell lysates can be used immediately or frozen and stored at $-70°$ C. until ready for use. The antigen can be used in a purified form or in partially purified or unpurified form as cell lysate. Alternatively, the antigen may be expressed by recombinant DNA techniques in any of a wide variety of expression systems.

In connection with enhancing an immune response to tumor antigens, in one embodiment, the invention provides a method for enhancing in an individual diagnosed with a tumor an immune response to an antigen expressed by the tumor. The method comprises administering to the individual, in an amount effective to enhance the immune response to the antigen, an agent capable of inhibiting SR-A, wherein the growth of the tumor is inhibited subsequent to administering the agent. Optionally, an antigen expressed by the tumor may also be administered to the individual.

In another embodiment, the invention provides a method for enhancing in an individual an immune response to a desired antigen comprising administering to the individual antigen presenting cells (APCs), such as dendritic cells, which have been exposed to the desired antigen and in which SR-A has been specifically inhibited. By dendritic cells in which SR-A has been specifically inhibited it is meant that the dendritic cells comprise and/or have been exposed to an agent that can specifically inhibit SR-A, in contrast to having been exposed only to an agent that elicits a more generalized inhibition of cellular processes, such as cellular division, transcription or translation. In performance of this embodiment, the dendritic cells may first be isolated from an individual using conventional techniques. The dendritic cells may be isolated from the individual in whom an enhanced immune response to a desired antigen is intended. The agent may be administered to the isolated dendritic cells so as to specifically inhibit SR-A in the isolated dendritic cells. The isolated dendritic cells may be also exposed to the desired antigen, such as by pre-loading the dendritic cells with the antigen protein or transfecting the cells with antigen encoding DNA. The isolated dendritic cells can be administered to the individual so as to elicit an enhanced immune response to the desired antigen. The dendritic cells administered to the individual may accordingly comprise the agent and/or the antigen upon administration to the individual.

In one embodiment, the invention provides a method for enhancing in an individual an immune response to a tumor by administering to the individual an effective amount of a composition comprising dendritic cells, wherein the dendritic cells are characterized by having specifically inhibited SR-A, and wherein administering the composition enhances the immune response to the tumor, such that the growth of the tumor is inhibited after administering the composition. The method may further comprise, prior to administration to the individual, exposing the dendritic cells to an antigen expressed by the tumor, and may also comprise the use of any conventional anti-cancer therapy. A preferred anti-cancer therapy is irradiation of cancer cells.

Inhibition of SR-A function using different approaches (e.g., antibodies, shRNA silencing or inhibitory molecules) may be utilized in different settings for promoting immune-mediated rejection or control of tumors. For example, isolated DCs in which SR-A has been inhibited can be loaded with antigens or transfected with antigen encoding cDNA or mRNA. The modified DCs may be administrated as vaccines into a host for generation of antigen-specific immune responses. This approach may also be used for augmentation of an immune response against antigens relavent to infectious diseases.

Tumor-bearing patients may be treated with other conventional therapies such as radiotherapy or chemotherapy, followed by in situ administration of DCs in which SR-A has been inhibited to the tumor site. It is expected that the DCs will capture antigens released from the damaged tumor and present the antigens to the host immune system for induction of a tumor-specific immune response.

In another embodiment, the host may be immunized with an antigen or tumor-specific vaccines and strategies to achive systemic or local SR-A inhibition in DCs can applied to the immunized host to improve vaccine efficacy.

In another embodiment, the invention provides a composition comprising substantially purified dendritic cells, wherein the dendritic cells are characterized by specifically inhibited SR-A expression and/or function. Such dendritic cells can be prepared by, for example, isolating cells from a host and substantially purifying the dendritic cells from other cell types using conventional techniques, and exposing the dendritic cells to an agent capable of specifically inhibiting SR-A. Such cells may be exposed to an antigen against which an enhanced immune response in the host is desired and introduced back into the host.

Specific embodiments of the invention are presented in the following Examples which are meant to illustrate but not limit the invention.

EXAMPLE 1

This Example provides a description of making SR-A (−/−) mice and the effect of knocking out SR-A in mice on immune responses to particular antigens.

The following materials and methods were used in obtaining the results presented in this Example.

Mice and Cell Lines

SR-A null mice (7) were backcrossed to the C57BL/6J mice (11) and were a generous gift of M. Freeman (Harvard Medical School) and B. Berwin (Dartmouth Medical School) (5, 11). Wild-type (WT) C57BL/6 mice were purchased from Jackson Laboratory (Bar Harbor, Me.). Mice were maintained in a specific pathogen-free facility at Roswell Park Cancer Institute. Animal care and experiments were conducted in accordance with institutional and National Institutes of Health (NIH) guidelines and approved by the Institutional Animal Care and Use Committee. B16 (F10) cells ($H-2^b$), a spontaneous murine melanoma from ATCC and D121 cell line ($H-2^b$), a subline of the Lewis Lung carcinoma provided by S. Ferrone at our institute, were maintained in DMEM, supplemented with 10% heat-inactivated fetal bovine serum (Life Technologies, Grand Island, N.Y.), 2 mM L-glutamine, 100 U/ml penicillin, and 100 μg/ml streptomycin.

Preparation of Tumor Cells for Vaccination

Tumor cells were treated by ionizing irradiation (IR) with 100 Gy in a $^{137}$Cs-irradiater or exposed to UV light (Stratalinker 1800, Stratagen, Inc., La Jolla Calif.) for 5 min. Cells were then washed and resuspended in PBS at $1\times10^7$ cells/ml. For preparation of cell lysate, tumor cells were suspended in PBS and subjected to four cycles of rapid freeze/thaw exposures and spun at 12,000 rpm at 4° C. for 10 min to remove cellular debris.

Tumor Studies

For tumor challenge study, mice (5 mice per group) were immunized s.c. with $1\times10^6$ irradiated tumor cells in the left flank. In some cases, the second boost was given one week later. Seven days after immunization, mice were challenged by s.c. injections of live B16 ($2\times10^5$ cells per mouse) or D121 tumor cells ($4\times10^5$ cells per mouse) into the right flank. For therapeutic studies, mice were inoculated with $2\times10^5$ D121 tumor cells or B16 tumor cells on day 0, followed by treatment with irradiated tumor cells on days 2, 4, 6, and 8. Tumor growth was monitored every other day. The tumor volume is calculated using the formula V=(The shortest diameter$^2$×the longest diameter)/2.

Enzyme-Linked Immunosorbent Spot (ELISPOT) Assay

Splenocytes were isolated from immunized mice or tumor-free mice to determine tumor-specific or antigen-specific IFN-γ secreting T cells using ELISPOT assay as previously described (12). Briefly, filtration plates (Millipore, Bedford, Mass.) were coated with 10 μg/ml rat anti-mouse IFN-γ antibody (clone R4-6A2, Pharmingen, San Diego, Calif.) at 4° C. overnight. Plates were then washed and blocked with culture medium containing 10% FBS. Splenocytes ($1\times10^6$/well) were incubated with the with 5 μg/ml $H-2K^b$ restricted CTL epitope $TRP2_{180-188}$ (SVYDFFVWL) (13) or $H-2D^b$ restricted CTL epitope $gp100_{25-32}$ (EGSRNQDWL) (14) in the presence of 10 U/ml IL-2 at 37° C. for 24 h. In some cases, irradiated B16 or D121 cells (splenocyte:tumor cell=20:1) were used as stimulators. Plates were then extensively washed and incubated with 5 μg/ml biotinylated IFN-γ antibody (clone XMG1.2, Pharmingen, San Diego, Calif.) at 4° C. overnight. After washes, 0.2 U/ml avidin-alkaline phosphatase D (Vector Laboratories, Burlingame, Calif.) was added and incubated for 2 h at room temperature. Spots were developed by adding 5-bromo-4-chloro-3-indolyl phosphatase/Nitro Blue Tetrazolium (Boehringer Mannheim, Indianapolis, Ind.) and incubated at room temperature for 20 minutes. The spots were counted using an ELISPOT counter (Carl Zeiss, Germany).

In Vivo Antibody Depletion

Depletion of $CD4^+$, $CD8^+$ T-cell subsets was accomplished by i.p. injection of 200 μg GK1.5 and 2.43 mAb respectively, given every other day for 6 days before immunization. Effective depletion of cell subsets was confirmed by FACS analysis of splenocytes 1 day before vaccination and maintained by the antibody injections twice a week for the duration of experiment. Isotype-matched antibodies were used as control. For functional inhibition of phagocytic cells, 1 mg of Carrageenan (type II; Sigma) in 200 μl PBS was administered by i.p. injection as described (15).

Phagocytosis Assay

Mice were injected intraperitoneally with 3% thioglycollate broth, and elicited macrophages were collected after 4 days by peritoneal lavage. Mφ were cultured in Dulbecco's modified Eagle's medium containing 10% fetal calf serum overnight, and non-adherent cells were removed by washing. Mφ prepared in this manner routinely stained positively for CD11b (>96%) by flow cytometry. UV treated tumor cells were labeled with 2 nM 5 (and 6)-carboxyfluorescein diacetate succinimidyl ester (CFSE, Molecular Probes, Eugene, Oreg.) in PBS at 37° C. for 5 min. Unbound dye was quenched by incubation with an equal volume of fetal bovine serum at 37° C. for 30 min. Cells were washed with complete medium and cocultured with thioglycollate-elicited Mφ at a 2:1 ratio for 4 h. Floating cells were washed off and adherent Mφ were collected and stained with CD11b-PE antibodies (PharMingen, San Diego, Calif.). Phagocytosis by Mφ was quantified by FACS with a B-D FACScaliber (Becton Dickinson) as the percentage of double positive staining cells.

Statistical Analysis

Tumor growth was analyzed using student's t test. Tumor-free mice were compared by the log-rank statistic analysis. Values of $p<0.05$ were considered significant.

By using the foregoing materials and methods, the following results were obtained.

Figure 2:
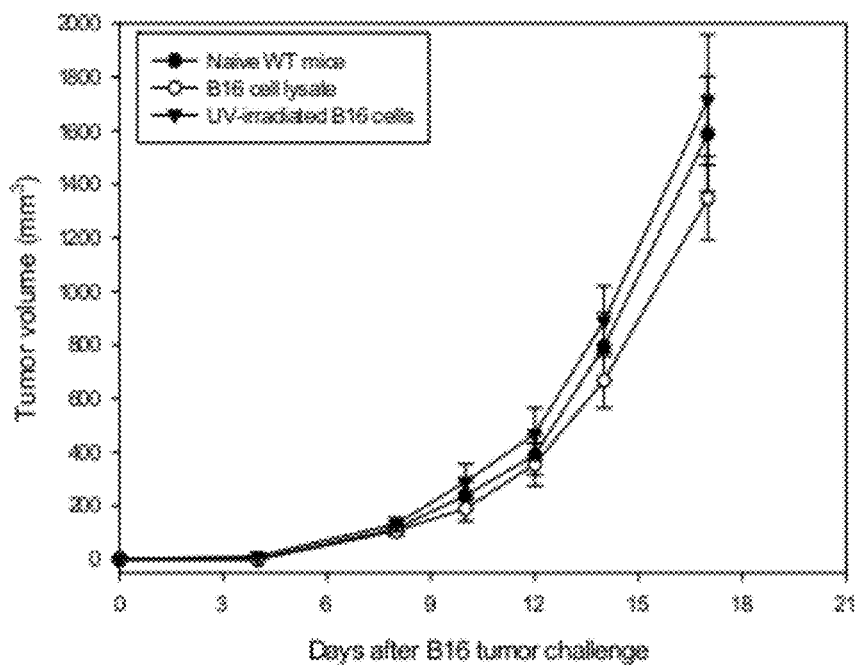
FIG. 2 provides a graphical representation of data demonstrating that UV-irradiated B16 melanoma cells provide a tumor protective effect in SR-A$^{-/-}$ mice. Mice (n=5) were immunized with UV-irradiated B16 cells, cell lysate derived from B16 cells or left untreated. One week later, mice were challenged with viable B16 tumor cells (2×10$^5$ cells) and followed for tumor growth (p<0.05, immunized SR-A$^{-/-}$ vs non-immunized SR-A$^{-/-}$ or immunized WT mice). The results shown represent three independent experiments performed.
Figure 2:
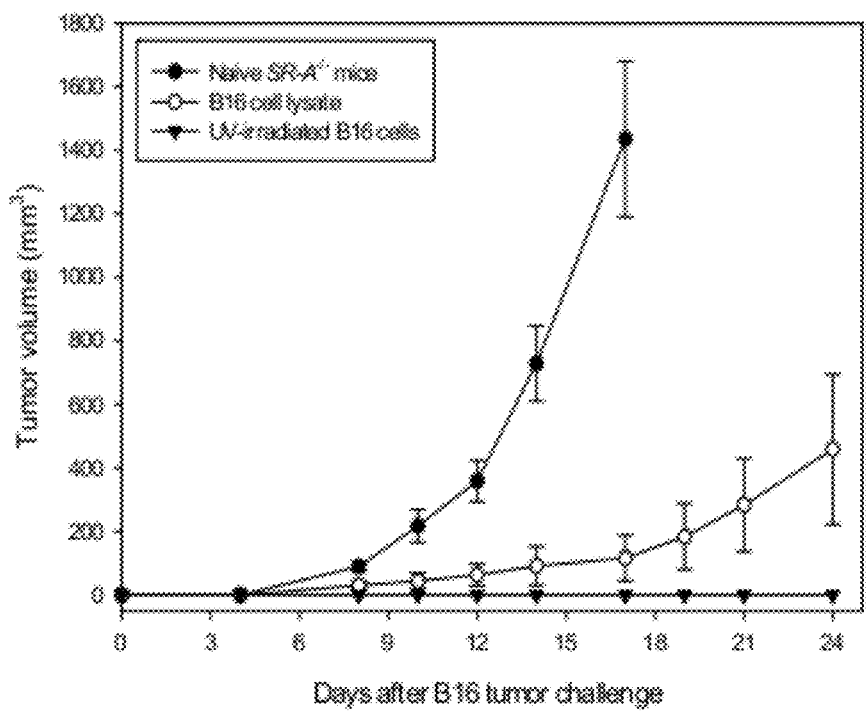

Vaccination with Irradiated Tumor Cells Results in Rejection of Poorly Immunogenic Tumor in SR-A$^{-/-}$ Mice A poorly immunogenic and highly metastatic tumor, D121 Lewis lung carcinoma (16, 17), was used to determine whether SR-A deficiency has an impact on tumor immunogenicity. Both wild-type (WT) C57BL/6 and SR-A$^{-/-}$ mice were immunized with ionizing irradiation (IR)-treated D121 tumor cells, followed by challenge with viable tumor cells one week later. As expected, WT mice immunized with or without IR-D121 cells developed aggressively growing tumors upon tumor challenge (FIG. 1. top panels). Strikingly, a single dose of immunization immunization with irradiated D121 tumor cells was able to completely protect SR-A$^{-/-}$ mice against subsequent tumor challenge, whereas D121 tumors inoculated in non-immunized SR-A$^{-/-}$ mice grew similarly as that in wild-type mice (FIG. 1. bottom panels). The tumor-free SR-A$^{-/-}$ mice were resistant to a secondary tumor challenge even after 8 months, suggesting an existence of a long-term immune memory (data not shown). The generality of the enhanced tumor-protective immunity was confirmed in another weakly immunogenic tumor, B16(F10) melanoma, which is of different histological origin (data not shown). Furthermore, a single dose of vaccination with UV-treated B16 tumor cells resulted in tumor rejection in this prophylactic setting in SR-A$^{-/-}$, not WT mice (FIG. 2), suggesting that radiation source does not affect on the immunogenicity of treated tumor cells. Although immunization of SR-A$^{-/-}$ mice with tumor lysate also significantly reduced tumor growth in SR-A$^{-/-}$ mice, all animals eventually developed tumors (FIG. 2).

Figure 3:
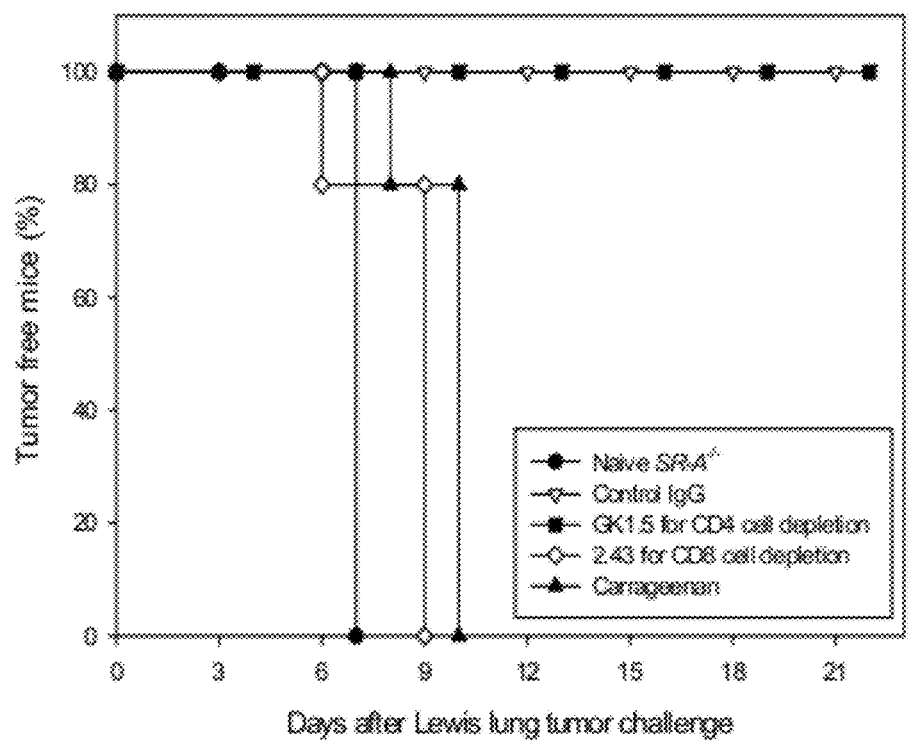
FIG. 3 provides a graphical representation of data showing that CD8$^+$ T cells are important for protective antitumor immunity in SR-A$^{-/-}$ mice. Depletion of subsets of T cells was performed by in vivo antibody injections prior to vaccination. Mice (n=10) were then immunized with irradiated D121 cells, followed by tumor challenge with viable D121 cells. Tumor incidence was monitored every other day (P=0.002 by the log rank test, CD8$^+$ T-cell depletion group vs IgG group; P=0.002, Carrageenan group vs IgG group; P>0.05, CD4$^+$ depletion group vs IgG group).

CD8$^+$ T Cells are Involved in the Protective Antitumor Immunity in SR-A$^{-/-}$ Mice The involvement of immune effector cells in the rejection of D121 tumor cells was examined by in vivo antibody depletion studies. Mice were depleted of CD4$^+$ or CD8$^+$ T-cell subset by treatment with anti-CD4 Ab GK1.5 or anti-CD8 Ab 2.43 prior to immunization. Depletions were more than 98% complete as assessed by FACS analysis of the splenic and lymph node populations (data not shown). Mice were then challenged with 4×10$^5$ D121 tumor cells (FIG. 3). Depletion of CD8$^+$ T cells completely abrogated the tumor protective immunity (p=0.002, vs IgG treated group), whereas depletion of CD4$^+$ T cells had no effect on the rejection of D121 tumor (p>0.05 vs IgG treated group). Carrageenan (15) was also used to deplete phagocytic cells during the priming phase. It was found that depletion of phagocytic cells also diminished the tumor protective effect (p=0.002, vs IgG treated group).

Figure 4:
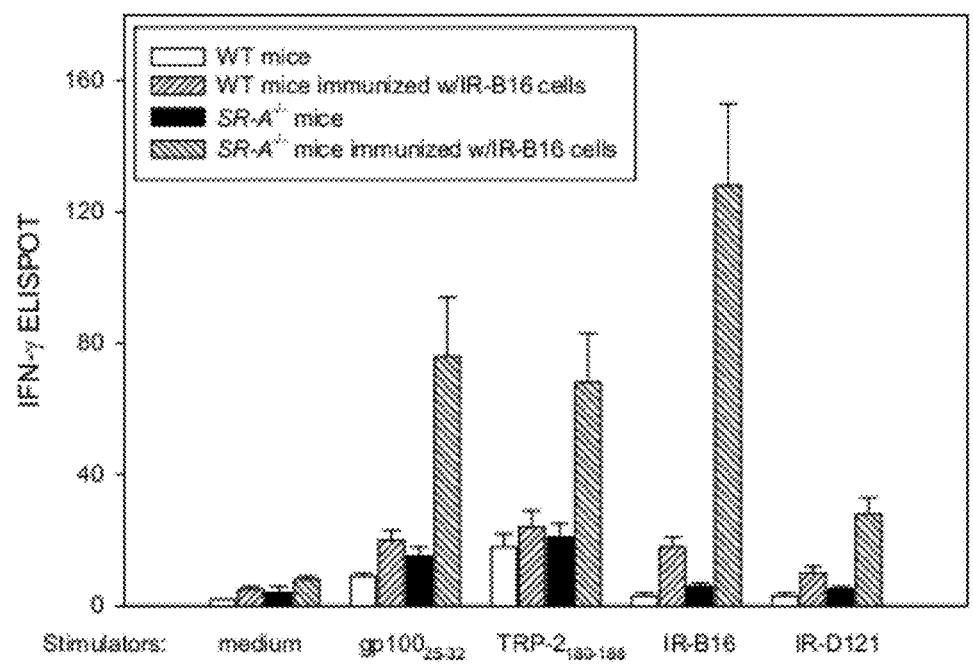
FIG. 4 provides a graphical representation of data showing that vaccination with irradiated tumor cells elicits antigen-specific cytotoxic T lymphocyte (CTL) responses in SR-A$^{-/-}$ mice. One week after immunization with irradiated B16 cells, splenocytes (1×10$^6$ cells) isolated from WT or SR-A$^{-/-}$ mice (n=3) were stimulated overnight with or without 5 μg/ml CTL epitopes gp100$_{25-32}$, TRP2$_{180-188}$ in the presence of 20 Um/L-2, or stimulated with either irradiated B16 cells or D121 cells. IFN-γ production was measured using ELISPOT assay. Representative data from three independent experiments are shown.

Vaccination with Irradiated Tumor Cells Elicits Antigen-Specific CTL Responses in SR-A$^{-/-}$ Mice B16 melanoma was used as a relevant model for evaluating immune responses specific for endogenous tumor antigens, since it expresses multiple melanoma associated antigens, including gp100 and TRP-2 (18). Following immunization with irradiated B16 tumor cells, splenocytes were isolated from WT or SR-A$^{-/-}$ mice and stimulated with CTL epitopes gp100$_{25-32}$ or TRP2$_{180-188}$. ELISPOT assay showed that splenocytes from the irradiated B16 cell immunized SR-A$^{-/-}$ animals displayed a robust antigen-specific IFN-γ production in compared to those from non-immunized mice or immunized WT mice (FIG. 4). In addition, the splenocytes from immunized SR-A$^{-/-}$ mice also produced high levels of IFN-γ when stimulated in vitro with irradiated B16 cells, not D121 cells, indicating a tumor specificity of primed CTLs.

Mφ from Both WT and SR-A$^{-/-}$ Mice Efficiently Phagocytose Dying Cells

Figure 5:
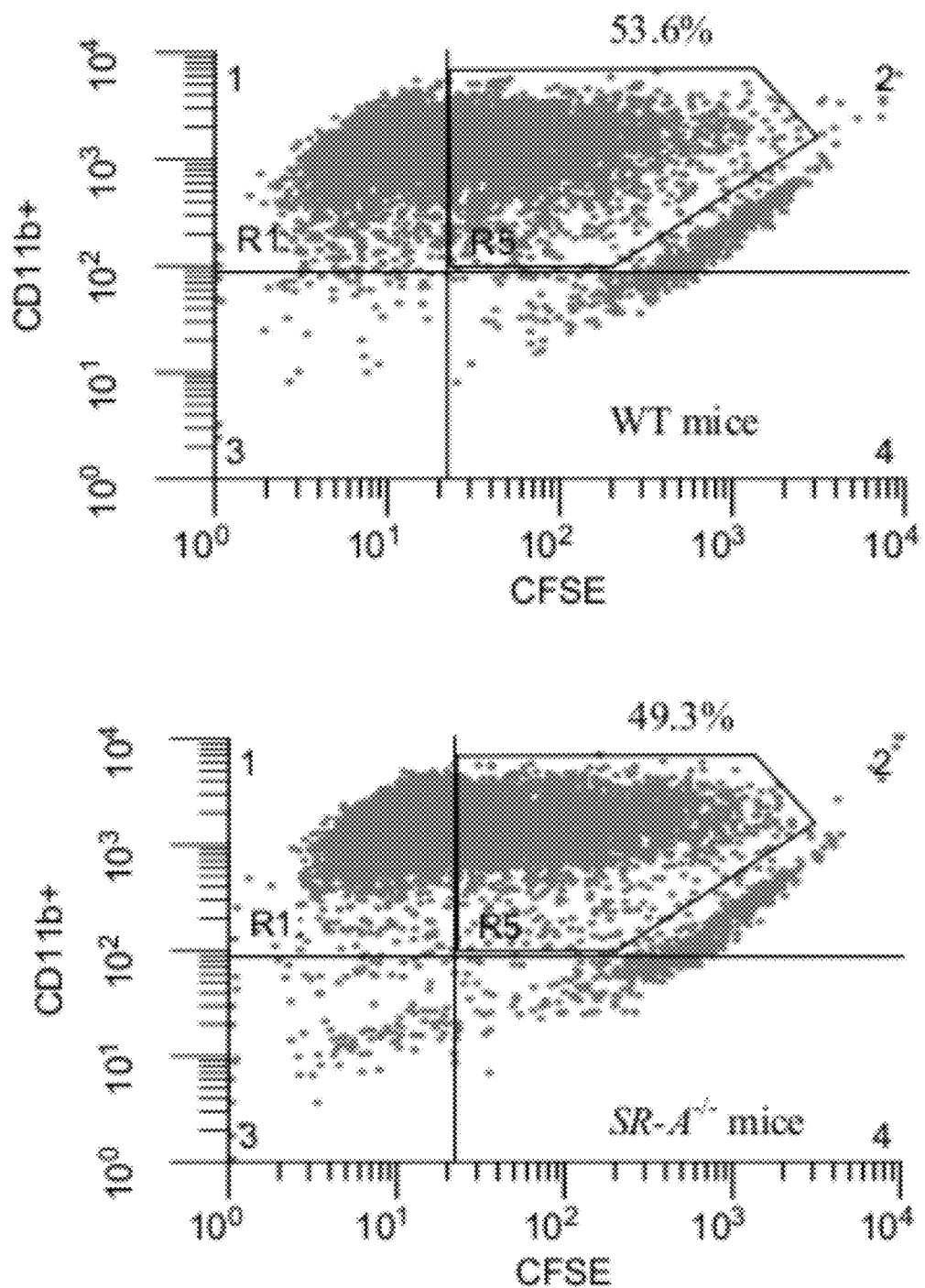
FIG. 5 provides a graphical representation of data demonstrating that Mϕ from both WT and SR-A$^{-/-}$ mice efficiently phagocytose apoptotic cells. UV treated D121 tumor cells were labeled with CFSE. Unbound dye was quenched by incubation with an equal volume of fetal bovine serum. Cells were washed and cocultured with thioglycollate-elicited Mφ at a 2:1 ratio for 4 h. Adherent Mφ were collected and stained with CD11b-PE antibodies. Phagocytosis by Mφ was quantified by fluorescence activated cell sorting (FACS) with a B-D FACScaliber as the percentage of double positive staining cells (p>0.05, Mφ from SR-A$^{-/-}$ vs Mφ from WT). The results shown represent three independent experiments.

Impairment of apoptotic cell phagocytosis can cause the breakdown of self-tolerance (19-21) and SR-A has been implicated in clearance of apoptotic cells (22). We compared the phagocytic capability of macrophages from SR-A$^{-/-}$ and WT mice. Phagocytosis was measured with FACscan analysis by detecting CD11b$^+$ Mφ that also contained CFSE. Quantification of phagocytic uptake indicated that Mφ derived from both mice efficiently engulfed dying tumor cells (p>0.05) (FIG. 5). The result was further confirmed by visualizing cells with fluorescence microscopy (data not shown), suggesting the presence of redundant receptors on APCs for dying cell clearance (23).

Figure 6:
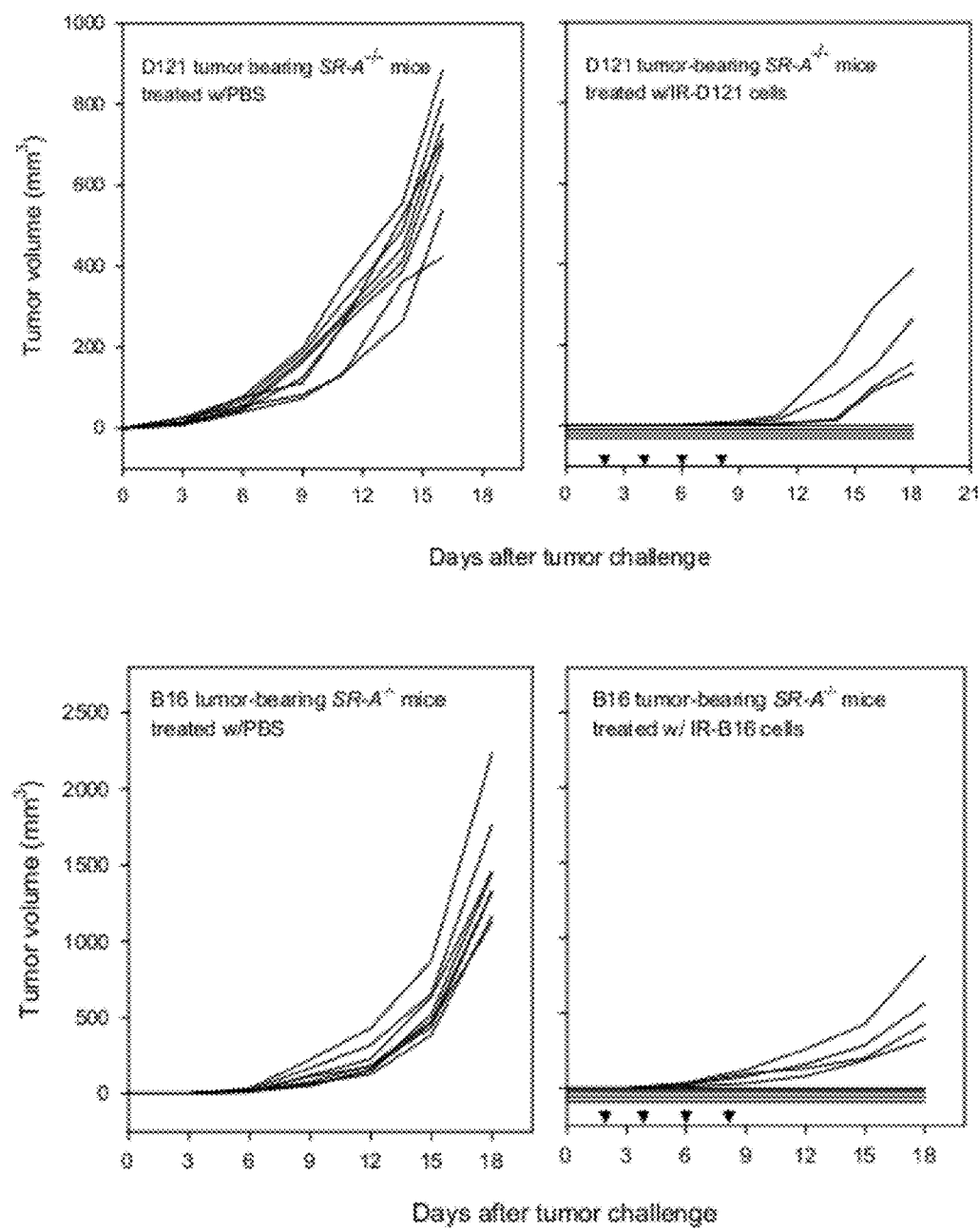
FIG. 6 provides a graphical representation of data demonstrating that treatment with irradiated tumor cells eradicates established tumor cells in SR-A$^{-/-}$ mice. Mice (n=8) were established with D121 Lewis lung tumor or B16 melanoma (2×10$^5$ cells) on day 0. Irradiated D121 cells or B16 cells were administered on days 2, 4, 6 and 8. Each curve represents tumor growth in each individual mouse (p<0.05, immunized SR-A$^{-/-}$ vs non-immunized SR-A$^{-/-}$). The results shown are from a representative experiment of three performed.

Treatment with Irradiated Tumor Cells Eradicates Established Tumor Cells in SR-A$^{-/-}$ Mice In view of the fact that prophylactic immunization resulted in tumor rejection in SR-A$^{-/-}$ mice, we determined therapeutic efficacy of vaccination in tumor-bearing mice. SR-A mice were first established with D121 tumor cells on day 0, and followed by treatment with irradiated D121 tumor cells on days 2, 4, 6 and 8. D121 tumor in the untreated SR-A$^{-/-}$ mice grew aggressively. However, administration of irradiated D121 cells resulted in a significantly reduced tumor growth rate and 50% of mice remained tumor free (FIG. 6, p<0.05 vs untreated group). A similar therapeutic effect was also seen in B16 melanoma model (FIG. 6).

Thus, the foregoing Example provides the first demonstration that SR-A negatively regulates antigen-specific antitumor immunity. The Example further demonstrates that administering an antigen to a mammal in which SR-A is inhibited results in an enhanced immune response to the antigen.

EXAMPLE 2

This Example demonstrates that the enhanced immune response to an antigen observed in SR-A –/– mice shown in Example 1 can be replicated by inhibition of SR-A in antigen presenting cells (e.g., dendritic cells) in wild type mice, and administering to the mice an antigen to which an enhanced immune response is desired.

Figure 7A:
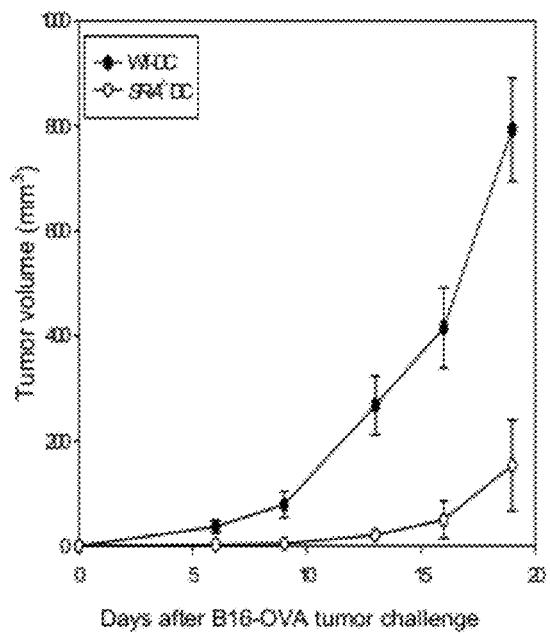
FIGS. 7A and 7B provide graphical representations of data demonstrating that SR-A deficient DCs stimulate antigen-specific tumor immunity more efficiently.

To first determine the contribution of dendritic cell (DC) to the SR-A absence enhanced vaccine potency observed in SR-A knockout mice, we compared the capability of Bone marrow (BM)-DCs from wild-type (WT) or SR-A knockout mice to stimulate antigen-specific antitumor immunity (FIG. 7A).

Figure 7B:
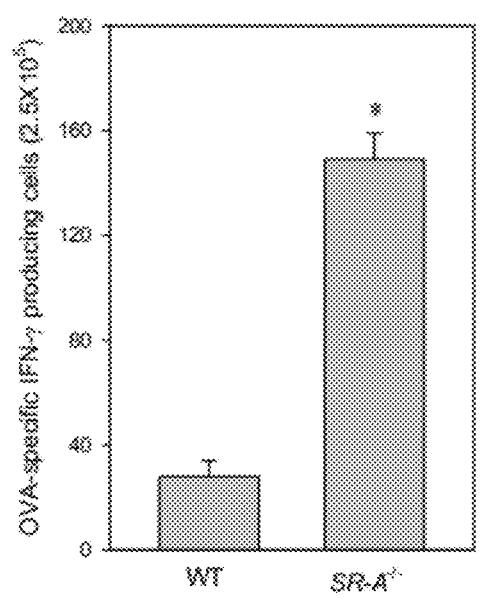

To obtain the results presented in FIG. 7, WT C57BL/6 mice were immunized with DCs pulsed with a model antigen ovalbumin (OVA), followed by tumor challenge with OVA-expressing B16 melanoma. The DCs were generated from bone marrow in the presence of GM-CSF and IL-4. Briefly, mouse BM cells were cultured at 37° C. in 5% humidified CO$_2$ with complete RPMI 1640 containing recombinant mouse GM-CSF (20 ng/ml; BD Bioscience), and recombinant mouse IL-4 (5 ng/ml; BD Bioscience). On days 2 and 4 of culture, the supernatant was removed and replaced with fresh medium containing GM-CSF and IL-4. Nonadherent cells from day 7 culture were incubated with OVA (10 µg/ml) for 3 h, followed by stimulation with 1 ng/ml LPS (*Escherichia coli* serotype 026:B6, Sigma-Aldrich, St. Louis, Mo.) for 16 h.

It was observed that SRA$^{-/-}$ DC were much more potent in controlling the growth of the poorly immunogenic B16 tumor compared to WT DC. Furthermore, we compared the ability of BM-DCs from both mouse strains to elicit an OVA-specific cytotoxic T-lymphocyte (CTL) response. Splenocytes from SR-A$^{-/-}$ DC-immunized mice produced much higher levels of IFN-γ upon stimulation with OVA-specific, MHC I-restricted CTL epitope (i.e., SIIMFEKL; SEQ ID NO:2), indicating that SR-A$^{-/-}$ DC are much more potent in priming an antigen-specific effector T-cell response compared to WT DC (FIG. 7A). These results thus demonstrate that SR-A negatively regulates immune activating functions of antigen presenting cells (APCs), particularly DCs, hence, providing a regulatory mechanism that allows DCs to control both innate and adaptive immunity.

Given our discovery of the inhibitory role for SR-A in the immunostimulatory functions of APC, we determined whether blocking or down-regulation (i.e., inhibition) of SR-A would improve vaccine potency mediated by DCs, which are generally considered the most important APCs for immune initiation.

Unlike most strategies used to generate immunopotent DCs in vitro through promoting DC maturation and co-stimulation, this approach seeks to remove the effect of the immunoinhibitory SR-A. Using lentiviral vectors for gene transfer and gene silencing by RNA interference (RNAi), we have examined whether silencing of endogenous SR-A in DCs enhances CTL activation and antitumor immunity.

RNA interference using shRNA can mediate effective sequence-specific silencing or downregulation of gene expression in mammalian cells. Self-inactivating lentiviral vectors (LV) are used to deliver RNAi because of their safety and superior transduction efficiency in both dividing and non-dividing cells, including hematopoietic stem cells and their progeny of terminally differentiated cells such as DCs (24).

Figure 8A:
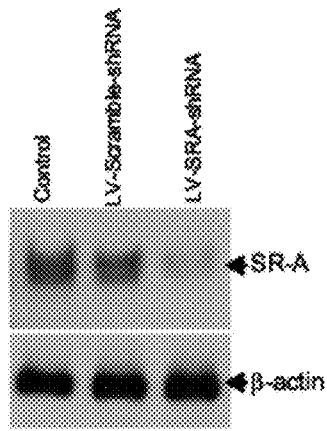
FIGS. 8A and 8B provide representations of data demonstrating that SR-A silenced DCs are highly potent in stimulating antigen-specific antitumor immunity.
Figure 8B:
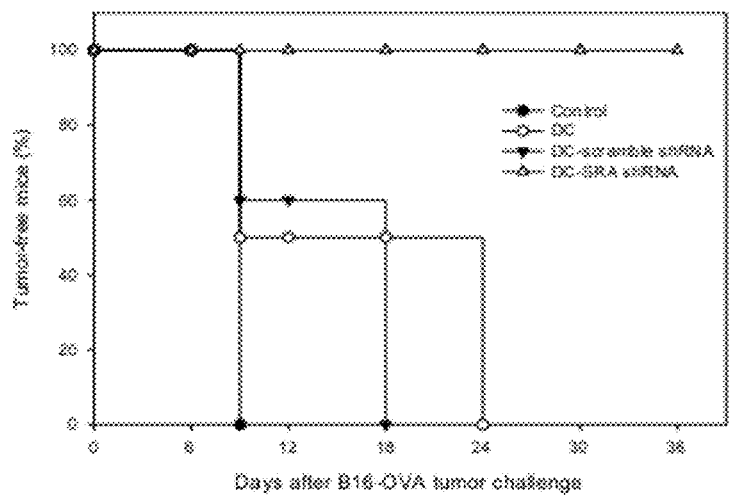
Figure 9A:
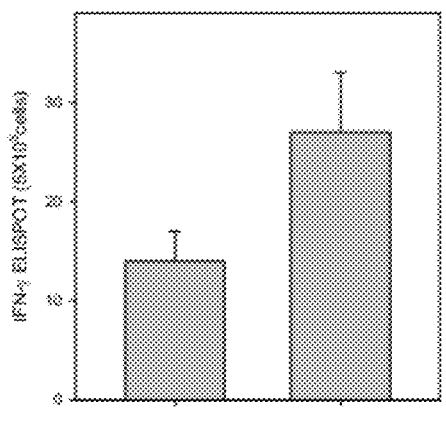
FIGS. 9A and 9B provide graphical representations of data demonstrating that SR-A silenced DCs are highly effective in eliciting an antigen-specific CTL response.
Figure 9B:
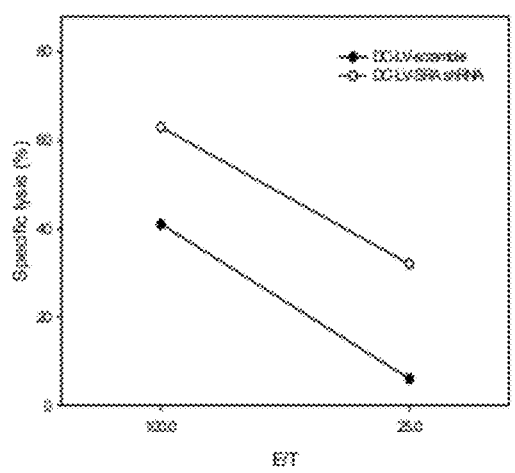

We designed and screened various lentivirus encoded short hairpin RNA (shRNA) to identify a shRNA that could down regulate SR-A expression. To perform the screening, non-replicated LV-SRA-shRNA was incubated with DCs at a ratio of 50:1 for 24 h at 37° C. We identified a small interfering RNA (siRNA) that specifically down regulates SR-A in DCs (FIG. 8A). As indicated by immunoblotting assays, the level of SR-A protein in DC1.2 cells infected with LV-SRA-shRNA to produce shRNA consisting of SEQ ID NO:1 was decreased by approximately 90%, compared with that in untreated or mock infected cells. Importantly, it was observed that SR-A down-regulated DCs, when loaded with soluable OVA antigen, were much more effective than control DCs treated with scramble shRNA in eradication of highly aggressive B16 tumor expressing OVA antigen (FIG. 8B). Moreover, we showed that SR-A down-regulation in DCs by RNA interference promoted an antigen-specific CTL response more effectively compared to the scramble shRNA, as indicated by higher levels of IFN-γ production in splenocytes upon stimulation with $OVA_{257-264}$ peptide (FIG. 9A) and enhanced cytolytic activity of OVA-specific effector $CD8^+$-T cell (FIG. 9B).

Thus, taken together, the data presented herein indicate that the functional differences in immune responses observed in WT and $SR-A^{-/-}$ mice are likely due to a direct effect of SR-A expression, rather than, for example, an alteration in the development of DCs in the absence of SR-A. Importantly, we have demonstrated that specifically inhibiting SR-A in DCs can enhance an immune response in a mammal against a desired antigen.

REFERENCES

1. Hughes, et al. Eur J Immunol 1995; 25:466-73.
2. Pearson et al. Chem Biol 1998; 5:R193-203.
4. Krieger et al. Curr Opin Lipidol 1997; 8:275-80.
5. Berwin et al. Embo J 2003; 22:6127-36.
6. Kodama et al. Proc Natl Acad Sci USA 1988; 85:9238-42.
7. Suzuki et al. Nature 1997; 386:292-6.
8. Thomas et al. J Exp Med 2000; 191:147-56.
9. Ishiguro et al. Am J Pathol 2001; 158:179-88.
10. Peiser et al. Infect Immun 2002; 70:5346-54.
11. Kunjathoor et al. J Biol Chem 2002; 277:49982-8.
12. Wang et al. Cancer Res 2003; 63:2553-60.
13. Bloom et al. J Exp Med 1997; 185:453-9.
14. Overwijk et al. J Exp Med 1998; 188:277-86.
15. Udono et al. Proc Natl Acad Sci USA 1994; 91:3077-81.
16. Sugiura et al. Cancer Res 1955; 15:38-51.
17. Popovic et al. Clin Exp Metastasis 1998; 16:623-32.
18. Engelhard et al. Immunological Reviews 2002; 188:136-46.
19. Bondanza et al. J Exp Med 2004; 200:1157-65.
20. Asano et al. J Exp Med 2004; 200:459-67.
21. Cohen et al. J Exp Med 2002; 196:135-40.
22. Platt et al. Proc Natl Acad Sci USA 1996; 93:12456-60.
23. Platt et all. J Immunol 2000; 164:4861-7.
24. Rubinson et al. Nat Genet. 2003; 33:401-6.

We claim:

1. A substantially purified population of mammalian dendritic cells, wherein the dendritic cells are characterized by specifically inhibited class A macrophage scavenger receptor (SR-A) activity, wherein the SR-A activity is inhibited by a polynucleotide having a sequence complementary to a nucleotide sequence encoding SR-A.

2. The substantially purified population of mammalian dendritic cells of claim 1, wherein the polynucleotide is an shRNA.

3. A composition comprising a purified population of mammalian dendritic cells of claim 1.

4. The composition of claim 3, wherein the composition further comprises an antigen.

5. The composition of claim 4, wherein the antigen is a tumor antigen.

6. A method for enhancing in an individual an immune response to a desired antigen comprising administering to the individual the desired antigen and, in an amount effective to enhance the immune response to the desired antigen in the individual, an agent capable of specifically inhibiting class A macrophage scavenger receptor (SR-A), wherein the agent comprises a polynucleotide having a sequence complementary to a nucleotide sequence encoding SR-A.

7. The method of claim 6, wherein the polynucleotide is an shRNA.

* * * * *

UNITED STATES PATENT AND TRADEMARK OFFICE
CERTIFICATE OF CORRECTION

PATENT NO. : 8,314,076 B2
APPLICATION NO. : 13/413177
DATED : November 20, 2012
INVENTOR(S) : Wang et al.

Page 1 of 1

It is certified that error appears in the above-identified patent and that said Letters Patent is hereby corrected as shown below:

In the Specifications

Column 1, lines 10-13 should read:

--STATEMENT AS TO FEDERALLY SPONSORED RESEARCH

This invention was made with government support under CA099326, CA129111 and CA121848 awarded by the National Institutes of Health. The government has certain rights in the invention.--

Signed and Sealed this
Ninth Day of July, 2013

Teresa Stanek Rea
*Acting Director of the United States Patent and Trademark Office*

SEQUENCE LISTING

<160> NUMBER OF SEQ ID NOS: 4

<210> SEQ ID NO 1
<211> LENGTH: 58
<212> TYPE: RNA
<213> ORGANISM: Mouse

<400> SEQUENCE: 1
ccgggcaguu cagaauccgu gaaaucucga gauuucacgg auucugaacu gcuuuuug     58

<210> SEQ ID NO 2
<211> LENGTH: 8
<212> TYPE: PRT
<213> ORGANISM: Chicken

<400> SEQUENCE: 2

Ser Ile Ile Met Phe Glu Lys Leu
1               5

<210> SEQ ID NO 3
<211> LENGTH: 9
<212> TYPE: PRT
<213> ORGANISM: Mouse

<400> SEQUENCE: 3

```
Ser Val Tyr Asp Phe Phe Val Trp Leu
1               5

<210> SEQ ID NO 4
<211> LENGTH: 9
<212> TYPE: PRT
<213> ORGANISM: Mouse

<400> SEQUENCE: 4

Glu Gly Ser Arg Asn Gln Asp Trp Leu
1               5
```